United States Patent [19]
Wiegleb et al.

[11] Patent Number: 5,391,891
[45] Date of Patent: Feb. 21, 1995

[54] MOISTURE SENSING DEVICE

[75] Inventors: Gerhard Wiegleb, Neuarnspach; Norbert Bendicks, Hemer; Berthold Esders, Schalksm, all of Germany

[73] Assignee: Leopold Kostal GmbH & Co. KG, Ludenscheid, Germany

[21] Appl. No.: 980,748

[22] Filed: Nov. 24, 1992

Related U.S. Application Data

[63] Continuation-in-part of Ser. No. 661,556, Feb. 26, 1991, abandoned.

[30] Foreign Application Priority Data

Feb. 28, 1990 [DE] Germany .............. 4006174

[51] Int. Cl.⁶ .......................................... G01N 15/06
[52] U.S. Cl. ...................... 250/574; 250/227.25
[58] Field of Search ............ 250/227.25, 574, 216; 318/483; 340/602

[56] References Cited

U.S. PATENT DOCUMENTS 4,152,070 5/1979 Kushner .................. 250/574
4,616,928 10/1986 Leavitte et al. ............ 250/574

FOREIGN PATENT DOCUMENTS 3532199 3/1987 Germany .
59-44641 3/1984 Japan .
59-85944 5/1984 Japan .

*Primary Examiner*—David C. Nelms
*Assistant Examiner*—K. Shami
*Attorney, Agent, or Firm*—Brooks & Kushman

[57] ABSTRACT

A sensor device which registers the amount of moisture on a transparent screen. The sensor is connected to at least one light conducting element which is provided on one side with at least one beam emitter and on the other side with at least one beam receiver. The light conducting element is provided with a layer of reflecting material to enable multiple reflection of the beam issuing from the beam emitter.

20 Claims, 5 Drawing Sheets

MOISTURE SENSING DEVICE

CROSS-REFERENCE TO RELATED APPLICATION

This is a continuation-in-part of application Ser. No. 661,556, filed Feb. 26, 1991, now abandoned.

BACKGROUND OF THE INVENTION

1. Field Of The Invention

The present invention relates to an improved sensor device for detecting liquid, preferably in drop form, on a glass screen such as a windshield.

2. Description Of The Related Art

Sensor devices of this type are particularly intended to register the amount of liquid present on the front or rear windshield of a motor vehicle in a directly related form and within a defined unit of time and then, depending on the degree of wetness, to automatically influence an associated windshield wiper system.

There has been previously described a control device for a windshield wiper motor, in which a light conducting element is attached to a windshield by means of light conducting adhesive and provided with a beam emitter and receiver. The beams are emitted and received via two lenses. The beam emitter and receiver are so arranged that any beam emitted from the output element of the emitter is at an angle of approximately 90° relative to the beam entering the input element of the receiver defined at the point where the beam enters or leaves the light conducting element.

In this version, in order to achieve multiple reflection of the beams, a reflector means is situated in an area which is between the two lenses, consisting of a part of the surface of the windshield which faces the light conducting element and an air space next to it. Here, however, the difficulty arises that the sensing area is small, and condensation settles on the reflector surface of the windshield out of the air space, because of temperature differences between the inside and outside of the windshield. This condensation then changes the reflective characteristics of the windshield, and the intensity of the beam entering the receiver is not a true indicator of the actual amount of rain or other liquid drops present on the windshield surface. It follows that the signal which is emitted from the receiver is not appropriate and than the windshield wiper system is not activated as intended.

A further sensor device variant is known in which the reflector means consists of a metal plate running through the light conducting element parallel to the windshield. With this design, however, haircracks can appear in the material of the light conducting element for the following reasons. The expansion coefficients of this material—glass, PLEXIGLASS or similar—and that of the metal plate reflector means, which is quite thick (approximately 1 mm) and preferably made of aluminum, are different, and the temperature to which a windshield-mounted sensor is exposed can vary between −40° to +90° C. Any haircracks can have a considerable effect on the path of the beams and also admits moisture, possibly in the form of dirty water. Total failure of the device can be the result.

During manufacturing, the cooling rates within the glass or plexiglass can also vary depending on the material's proximity to the cold metal plate reflector means in the tool, leading to tensions and again, later cracking or splitting between the plate and the main material, with resultant beam and signal distortion. These problems can be reduced if the reflector plate is made thinner, but this is only possible to a limited extent, as the plate must be capable of being precisely held in the tool and must not deform when the material of the light conducting element is applied.

SUMMARY OF THE INVENTION

The present invention aims to overcome these disadvantages and to improve on known types of sensor devices in order to enable optimum functioning at differing inside and outside windshield temperatures while being relatively simple to manufacture, especially as regards the reflector means.

The sensor device of the present invention detects the amount of moisture on a transparent screen. The device comprises at least one light conducting element, which affords a relatively wide sampling area upon which moisture may be sensed. The at least one light conducting element is affixed to a side of the screen which is not exposed to moisture. At least one pair of lenses is associated with each light conducting element. Each pair of lenses is in optical communication with a beam emitter and a beam receiver. Each emitter and its associated receiver are spatially separated from each other in a horizontal plane. Each pair of lenses comprises a first lens through which the emitted beam passes, the first lens being configured for reducing the dispersion of a divergent beam generated by the beam emitter. A second lens is mounted on the light conducting element, through which a reflected beam passes. The second lens focuses the reflected beam towards the beam receiver.

A reflective material layer is applied directly to the light conducting element and substantially covers a side thereof which is remote from the transparent screen.

The emitter and receiver are arranged in such a way that beams issuing from the emitter are reflected from the screen with an intensity which depends on the amount of moisture thereupon and are then reflected back and forth between the reflective material layer and the screen before passing through the associated second lens to the beam receiver. The beam receiver issues a signal which is in inverse proportion to the amount of moisture on the screen.

The precise characteristics which distinguish this sensor device from its forerunners will be apparent from the description below. A particular advantage of the present invention is that haircracks or other material distortions do not occur in the glass or PLEXIGLASS, as beam reflection is effected by means of a very thin reflective layer which is able to absorb differences of temperature and which is directly applied on the light conducting element. For this reason also, moisture cannot enter and damage the device.

It is very advantageous to equip a sensor device of this type with a means particularly aimed at heating the light conducting element. With such a heating means, the complete sensor device can be brought to a predefined temperature, for example 40° C., within a relatively short time. Temperature-induced inaccuracy is less likely, and at the same time, the windshield is partially warmed, so that snowflakes on the windshield are melted and can be detected as water drops.

Further objects and advantages of the invention will appear from the following detailed description, taken in conjunction with the accompanying drawings.

BRIEF DESCRIPTION OF THE DRAWINGS

FIG. 1a is a cross-section of a sensor device, taken along line A—A of FIG. 1d;

FIG. 1b is a cross-section of the sensor device, taken along line B—B of FIG. 1d;

FIG. 1c is a cross-section of the composite sensor device, taken along line C—C of FIG. 1a;

FIG. 1d is a top view of the composite sensor device of FIG. 1c;

DETAILED DESCRIPTION OF THE PREFERRED EMBODIMENTS

Figure 1:
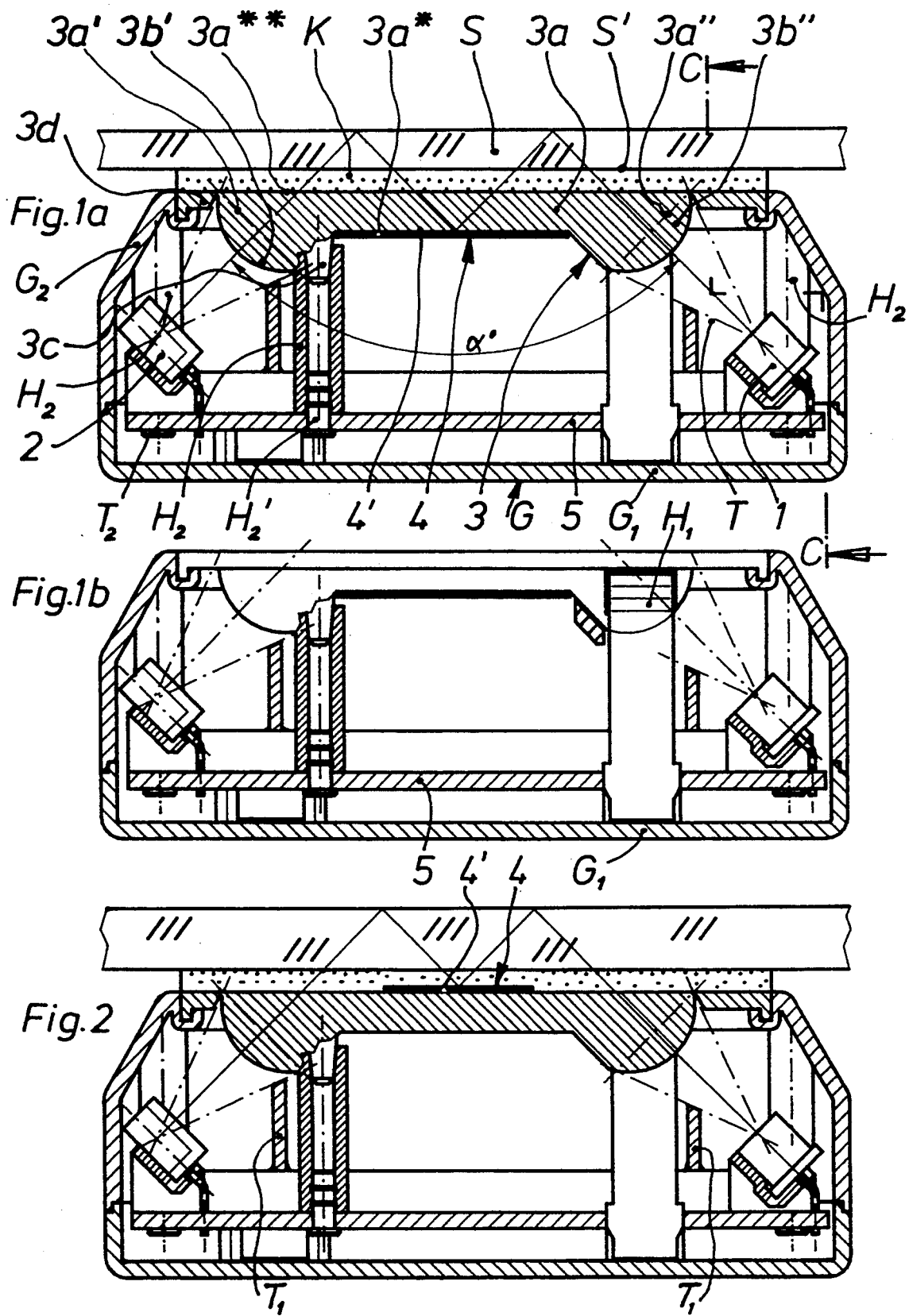

In the drawings, a sensor device is shown, which is intended to detect the amount of liquid present on a windshield, particularly in drop form. The sensor device consists basically of a light conducting element 3 which is provided on one side with a beam emitter 1 and on the other side with a beam receiver 2. This light conducting element is attached to the surface S' of the screen S which is not exposed to liquid with light conducting adhesive K. Screen S is preferably the windshield of a motor vehicle.

The sensor device, contained in housing G, is positioned on the windshield in a suitable position; i.e., so that it can detect liquid effectively while not limiting the driver's view.

The light conducting element 3 consists of a main body 3a which is basically trapezoidal in shape. However, the main body 3a can be of various shapes without departing from the scope of the invention. The main body 3a has side faces 3a' and 3a" which are each provided with a beam lens 3b', 3b". Surfaces 3a' and 3a" are of equal size and are angled in such a way that the center lines of the two lenses 3b' and 3b" are displaced at an angle of 90° in relation to one another. In this example, the lenses are formed as one piece with the main body 3a. It is also possible, of course, to attach the lenses to surfaces 3a', 3a" with light conducting adhesive and a centering pin to ensure correct orientation.

On the surface $3a^*$ of the main body 3a opposite to the surface which is attached to the windshield S there is a very thin material layer 4 (shown out-of-scale—i.e. larger—in the drawings), which serves to enable multiple reflection of the beams emitted from beam emitter 1.

This material layer is applied over an area between the two faces of the light conductive element 3a on which the lenses 3b', 3b" are affixed and runs parallel to the screen S. To enable optimum reflection, the material is preferably purest high-grade aluminum or copper and the surface 4' which faces towards screen S is highly polished. The material layer 4 is attached to light conducting element 3 over its whole area, preventing any air penetration between material layer 4 and the light conducting element 3 which could cause condensation to form on surfaces 4' or $3a^*$.

Figure 2:
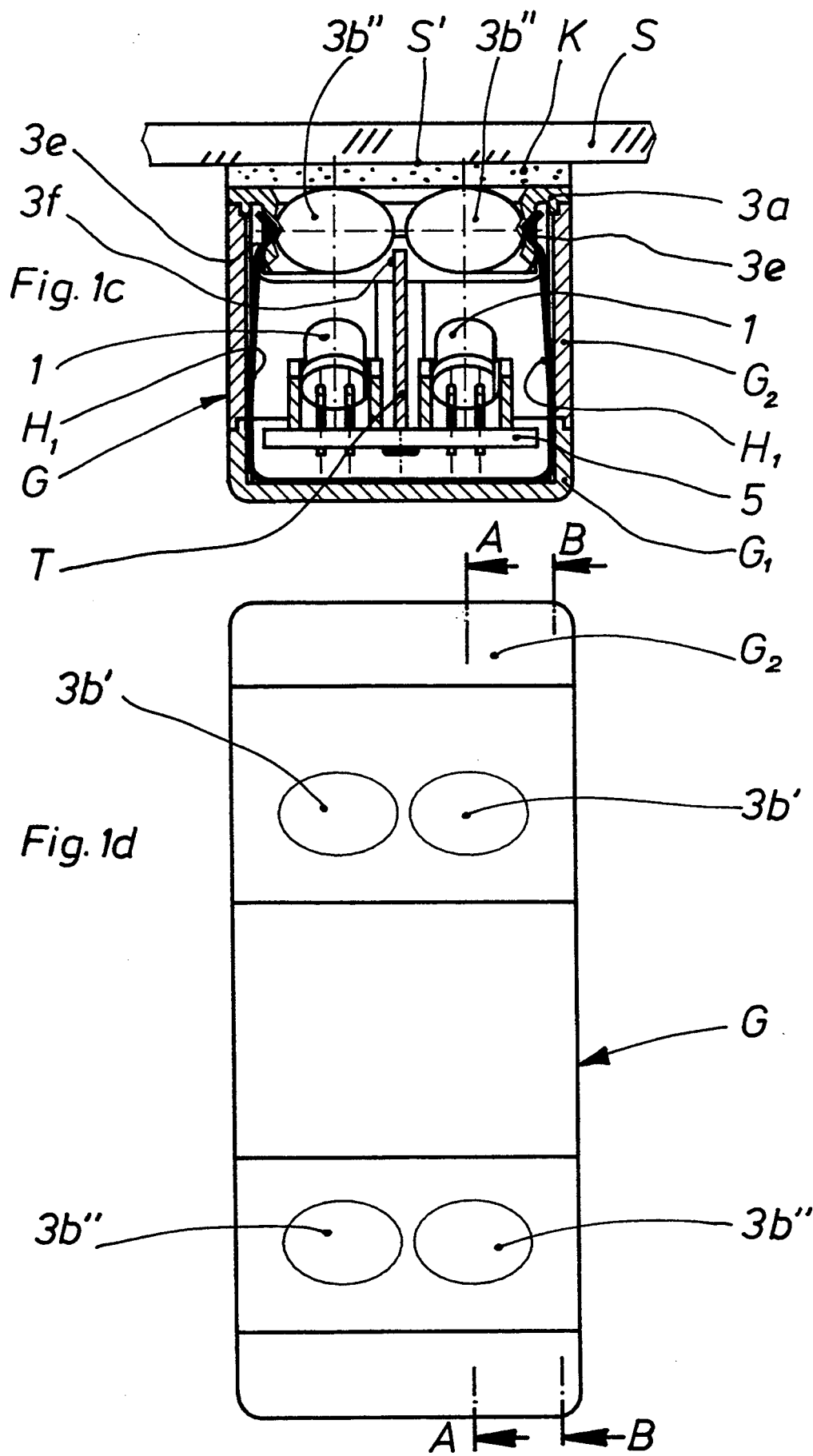
FIG. 2 is a cross-section of a further sensor device, taken along line A—A of FIG. 1d.

Material layer 4 can either be in the form of metal foil, metal-coated plastic foil or can be directly applied to the light conducting element 3 by means of thin-film technology and can of course, as shown in FIG. 2, also be applied to surface $3a^{**}$ of the main body 3a, which is directly next to the screen. In this latter case, the highly polished surface 4' of material layer 4 is optically connected to the screen S by means of light conducting adhesive K.

If this form is chosen, light conducting element 3 can be made considerably smaller because of the resultant shorter beam travel. Alternatively, if a light conducting element 3 of the same size as previously described is used, the device can function effectively in conjunction with a thicker screen than would be possible with the metal layer applied to the opposite surface $3a^*$ (see FIG. 2).

It is advantageous if the sensor device is provided with a heating system which particularly acts on the light conducting element. Such a heating device could consist, for example, of a PTC resistor. For reasons of simplicity, the heating device is not shown in the drawing.

The main body 3a of the light conducting element 3, which is attached to windshield S by means of light conducting adhesive K is connected to housing G with securing means. Housing G consists of a lower part G and, an upper part G2 and is preferably made of plastic material. The securing means consists of a U-shaped sprung retaining clip H1 (FIG. 1c) and equivalent recesses 3e in main body 3a of the device.

Furthermore, main body 3a is provided with blunt cones 3c which are molded or otherwise affixed on the surface facing away from windshield S. On these blunt cones, hollow cylindrical retaining means H2 are press-fitted at one end. At their other end, they are fixed to a printed circuit board to which beam emitter 1 and beam receiver 2 are electrically and, if desirable, mechanically connected. The cylindrical retaining means and the printed circuit board can be mechanically connected, as here for example, by press pins H2'.

In addition, light conducting element 3 is provided with a lip 3d running round all of its sides, which fits into an equivalent groove in the upper part of housing G2. This design prevents the ingress of air into the sensor device to a considerable extent and thus protects the lenses or other areas from being coated with airborne pollutants such as tobacco smoke and plastic vapor. A further advantage is that stray beams from the environment are prevented from entering the device through the join. It would, of course, also be possible to seal the join with appropriate sealing means.

A particularly advantageous form of the invention, aimed at increasing the field of measurement of the device, can be seen in FIGS. 1c and 1d. Here, several (two) light conducting elements 3 are combined to form a one-piece composite element with a common material layer 4. Light conducting separation of the single light conducting elements 3, which are each provided with a beam emitter 1 and a beam receiver 2, is achieved by means of dividing wall T, which is part of the upper housing G2 and which fits into a groove 3F of the main body 3a. Further dividing walls T1 are also provided for the purpose of reducing unwanted beam reflection within the device.

The preferred beams employed in the sensor device are either visible light or infra-red beams, with the emitter in the form of a light-emitting diode and the receiver in the form of a photo diode.

The emitter is preferably a flat light-emitting diode which emits beams over an angle of about 40° from the optical center line L. Emitter beams then impinge upon the lens $3b''$ (FIG. 1a). The lens $3b''$ is preferably an elliptic lens (see FIGS. 1c–1d) which parallelizes the beam before transmission through the main body $3a$, before refocusing by another elliptical lens $3b'$ which converges beams toward the beam receiver 2.

The light conducting adhesive K should be selected such that its refractive index is about 1.5. As a result of the parallelization and subsequent convergence of infrared rays, more infra-red energy is available to be sensed by the beam receiver 2, such that a widened moisture sensing surface is available on the windshield S.

The flat LED beam emitter 1 is coplanar with the major axis of the elliptical lens $3b''$ in order to optimize the intensity of beams available for moisture sensing. One such beam emitter 1 is manufactured by Siemens (SFH402 series) (GaAs infra-red emitter).

As noted above, a heating system can usefully be deployed within the invention as disclosed. Such a system can include, for example, a PTC resistor which is in thermal communication with the light conducting element. A PTC resistor is a self-regulating device which does not rely on an external measuring system to switch on or off. It is automatically "on" when the system is activated and switches off automatically when the required temperature has been reached.

Noteworthy also is that the disclosed heating system acts on the light-conducting and other sensor elements—not only on the windshield.

The location of the heating system in relation to the light-conducting element prevents temperature-induced faults in the sensor components. Additionally, its location also keeps the optical system free of fogging to prevent misting of the lenses, in particular, from interfering with beam transmission.

Preferably, the disclosed heating system is specifically adapted for a moisture sensing device including lenses and a light conducting element 3 which should ideally be kept optically clear.

In operation, the beam emitter 1 and beam receiver 2 are in the form of surface mounted device components for ease in assembly and compactness.

Preferably, the common material layer 4 is an aluminum or copper reflective layer wherein the reflection characteristics are well adapted to wavelengths in use in the disclosed invention. Such surface characteristics can be quantified as being in the range of 900 plus or minus 20 nanometers.

Figure 3:
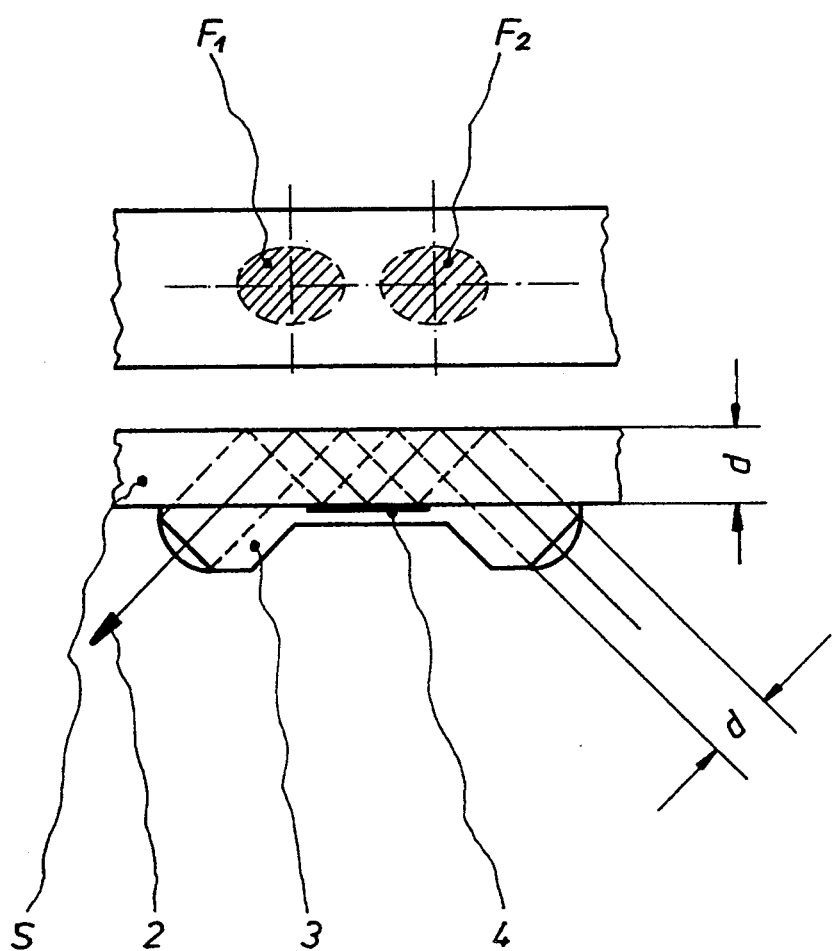
FIG. 3 is a cross-section of the sensor device depicting two independent measuring areas.

Turning now to FIG. 3, there is depicted the light conducting element 3 with the reflecting layer 4 located on the upper side. The body 3 is attached to the screen S of a given thickness "d". In this configuration, it is only possible to effectively use a beam of approximately the same width "d" in order to produce two independent measuring areas F1, F2. Independent measuring areas are necessary to avoid falsification of the signal received by the beam receiver 2. The width of F1 and F2 is necessarily quite small—approximating dimension "d". The length is approximately 1.41 times "d".

Figure 4:
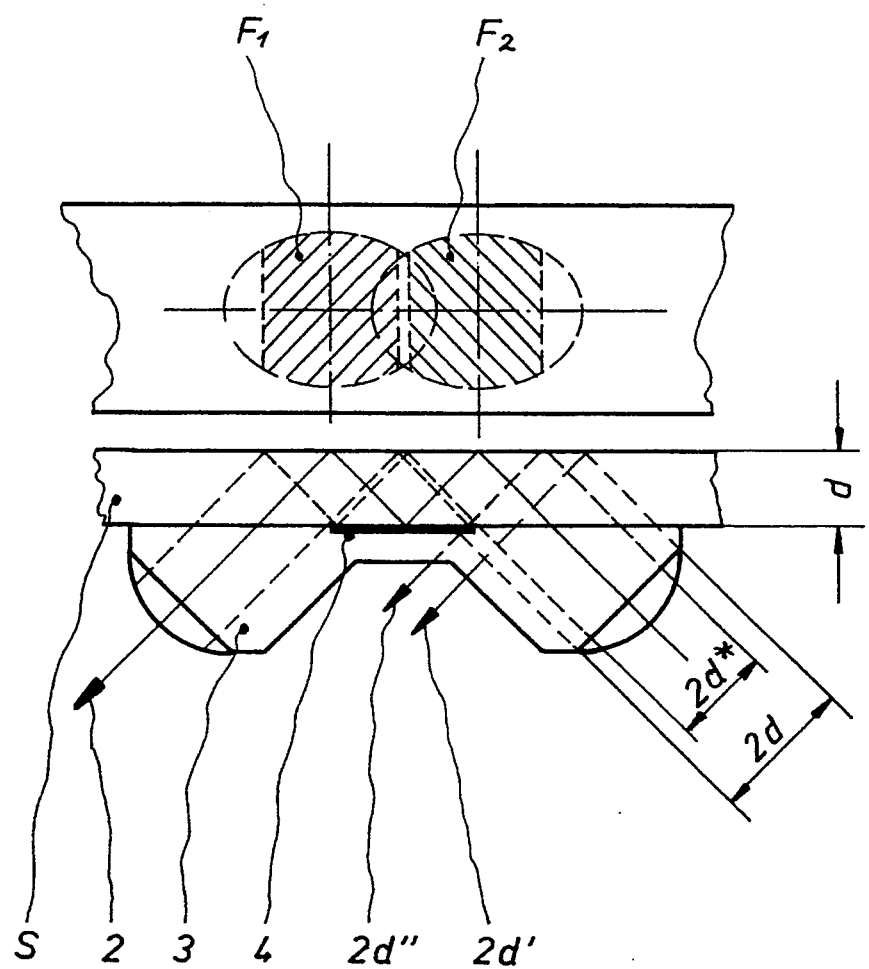
FIG. 4 is a cross-section of the sensor device wherein a wider beam is used for moisture sensing illustrating an overlap in measuring areas.

In FIG. 4, a wider beam of width $2d$ is used for moisture detection, where "d" is the width of the screen S. In the configuration depicted, the reflective layer 4 is on the first side of the light conducting element. In this configuration, only a fraction of the beam $2d^*$ reaches the beam receiver 2. This is because on the one hand, a portion $2d'$ of the beam is dissipated without striking the reflective layer 4. Also, another portion $2d''$ of the beam is blocked by the underside of the light conducting element 3.

In the configuration depicted in FIG. 4, the measuring areas F1, F2 overlap. This has a negative effect on measuring accuracy, because incoming, already reflected in outgoing light beams become mixed. The resulting signal cannot clearly be interpreted.

Figure 5:
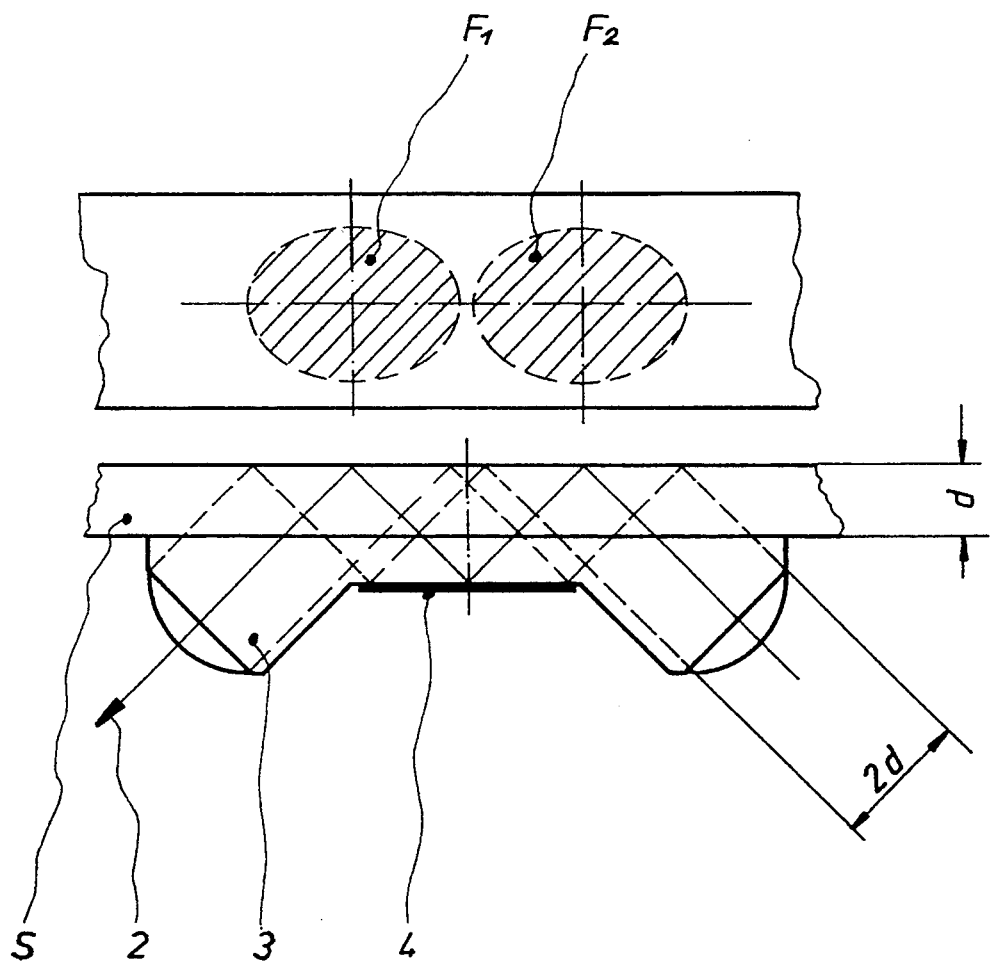
FIG. 5 is a cross-section of the sensor device wherein the reflective layer is located on the underside of the sensor body and wherein the whole of a wider sensing beam is used to produce two relatively large measuring areas.

Turning now to FIG. 5, the reflective layer 4 is located on the underside of the sensor body 3. In that configuration, the whole of the wider beam of width $2d$ can be used with a windshield of thickness "d" to produce two relatively large measuring areas F1, F2 which are independent to each other. This affords a wider sampling area and reduces the possibility of spurious resulting signals.

What is claimed is:

1. A sensor device for detecting the amount of moisture on a transparent screen, comprising:
    at least one light conducting element;
    means for affixing the at least one light conducting element to the screen on the side thereof which is not exposed to the moisture, each of said at least one light conducting elements having associated therewith
    at least one pair of lenses,
    a beam emitter, and
    a beam receiver, the emitter and receiver being spatially separated from one another in a horizontal plane, each of the at least one pair of lenses comprising a first lens through which an emitted beam passes, the first lens being configured for reducing the dispersion of a divergent beam generated by the beam emitter, and a second lens through which a reflected beam passes, the second lens serving to focus the reflected beam towards the beam receiver; and
    a reflective material layer applied directly to said light conducting element, substantially covering the side thereof which is remote from the transparent screen, such coverage and location allowing a wider beam to be effectively used for a given screen thickness, thereby permitting a larger measuring area for detecting the amount of moisture thereon than would be possible if the reflective material layer were applied on a side of the light conducting element which faces the screen;
    the emitter and receiver being arranged in such a way that beams issuing from the emitter are reflected from the screen with an intensity which depends on the amount of moisture thereupon and are then reflected between reflective material layer and the screen before passing through an associated second lens to the beam receiver,
    said beam receiver issuing a signal which is in inverse proportion to the amount of moisture on said screen.

2. The sensor device of claim 1, wherein said material layer has a thickness within the range of 0.1 to 10 microns.

3. The sensor device of claim 2, wherein at least one (4') of the two surfaces of said material layer (4) comprises metal and faces said screen (S).

4. The sensor device as in claim 3, wherein said material layer (4) comprises metal foil.

5. The sensor device of claim 3, wherein said material layer (4) comprises metal-coated plastic foil.

6. The sensor device of claim 3, wherein the metal portion of said material layer (4) comprises purest aluminum and the surface of the layer (4') which faces the screen (S) has a highly polished finish.

7. The sensor device of claim 3, wherein said material layer (4) comprises copper.

8. The sensor device of claim 3, wherein a common material layer (4) is applied to one or more of said at least one light conducting element (3), which is combined to form an integrated unit having a plurality of light conductors, while remaining optically separate.

9. The sensor device of claim 1, wherein the lenses and the light conducting element are formed into one piece.

10. The sensor device of claim 1, wherein the beam issuing from the emitter is oriented perpendicularly to the beam entering the receiver.

11. The sensor device of claim 1, wherein each pair of the at least one pair of lenses comprises:
a first elliptical lens through which the emitted beam passes, the first lens being adapted for producing a beam which becomes incident on the screen, and;
a second elliptical lens through which the reflected beam passes, the second lens being adapted to receive the reflected beam from the screen so that the reflected beam is converged by the second lens towards the beam receiver.

12. The sensor device of claim 11, wherein each elliptical lens includes:
a major axis;
each beam emitter generating a planar beam, the planar beam being parallel to the major axis of the associated elliptical lens.

13. The sensor device of claim 11, wherein
the transparent screen has a thickness which is approximately half the major axis of each elliptical lens.

14. The sensor device of claim 1, wherein the beam emitter generates visible light.

15. The sensor device of claim 1, wherein the beam emitter generates infra-red radiation.

16. The sensor device of claim 1, wherein the beam emitter comprises a light-emitting diode.

17. The sensor device of claim 1, wherein the receiver comprises a photodiode.

18. The sensor device of claim 1, also including a heating system in thermal communication with the transparent screen.

19. The sensor device of claim 1, further including a heating system in thermal communication with the light conducting element.

20. The sensor device of claim 1, wherein:
each pair of lenses is associated with a measuring area which is independent of a measuring area with which another pair of lenses is associated to avoid falsification of signals generated in response to moisture on the screen.

* * * * *